US00PP13872P29

(12) United States Plant Patent
Whetman

(10) Patent No.: US PP13,872 P2
(45) Date of Patent: Jun. 10, 2003

(54) DIANTHUS PLANT NAMED 'VALDA KITTY'

(76) Inventor: John Whetman, Deer Park Farm, Chudleigh, Devon (GB), TQ13 ONH ( * ) Notice: Subject to any disclaimer, the term of this patent is extended or adjusted under 35 U.S.C. 154(b) by 0 days.

(21) Appl. No.: 10/001,164

(22) Filed: Dec. 1, 2001

(51) Int. Cl.[7] ..... A01H 5/00

(52) U.S. Cl. ..... Plt./283

(58) Field of Search ..... Plt./283, 278

(56) References Cited

PUBLICATIONS

The New Royal Horticultural Society Dictionary of Gardening, vol. 2, Editor–in–Chief Anthony Huxley, The Stockton Press, New York, 1992, pp 50–56.*

EuroAmerican News, http:www.euroamprop.com/news/rhs–award.html, 2000, pp 1–3.*

* cited by examiner

*Primary Examiner*—Bruce R. Campell
*Assistant Examiner*—Anne Marie Grünberg

(57) ABSTRACT

A new cultivar of Dianthus named 'Valda Kitty' that is characterized by double, crimson red flowers, a compact habit and gray-green foliage. In combination these traits set 'Valda Kitty' apart from all other existing varieties of Dianthus known to the inventor.

2 Drawing Sheets

CROSS-REFERENCES TO RELATED APPLICATIONS

The application for this new invention is co-pending with three other applications entitled 'Valda Judith', 'Valda Louise' and 'Valda Isolde'. All are derived from the same program, having the same inventor and filing date as the present application entitled Dianthus 'Valda Kitty'.

Botanical classification: *Dianthus Allwoodii.*
Variety denomination: Valda Kitty.

BACKGROUND OF THE INVENTION

The present invention relates to a new and distinct cultivar of Carnation that is grown for its crimson flowers. The new cultivar is known botanically as *Dianthus Allwoodii* and will be referred to hereinafter by the cultivar name 'Valda Kitty'.

'Valda Kitty' is the product of a program conducted by the inventor in a cultivated area of Dawlish, Devon, England. The primary focus of the program was to select a variety of flower color mutations from the parent plant 'Valda Wyatt' (unpatented).

In 1995, a naturally occuring color sport mutation was found by the inventor on part of a petal of Dianthus 'Valda Wyatt' (not patented). The shoots on the lower part of the stem on which the color mutation occured were removed, rooted and grown out into flowers. One or two of the plants produced a whole flower exhibiting the mutated color. This process was repeated until a whole plant was obtained that produced the new color on all flowers.

'Valda Kitty' is a hardy perennial grown for its use as a container and landscape plant.

'Valda Kitty' was selected for its double, crimson flowers and is characterized by gray-green foliage, compact habit, profuse flowering, free flowering, long flowering and vigorous growth. It is distinguishable from the parent plant 'Valda Wyatt' by flower color. The flowers of 'Valda Wyatt' are more red (68B) with a incomplete ring (66B) around the base of the petal than those of 'Valda Kitty'. Asexual reproduction of the new cultivar was first accomplished by the inventor who took cuttings in a cultivated area of Dawlish, Devon, England in 1995. Since that time the characteristics of the new cultivar have been determined stable and are reproduced true to type in successive generations.

SUMMARY OF THE INVENTION

The following traits have been repeatedly observed and represent the characteristics of the new cultivar. These traits in combination distinguish this cultivar from all other commercial varieties known to the inventor. 'Valda Kitty' has not been tested under all possible conditions and phenotypic differences may be observed with variations in environmental, climatic and cultural conditions.

1. Dianthus 'Valda Kitty' reaches approximately 46 cm. in height and 38 cm. in width at 12 months.

2. Dianthus 'Valda Kitty' exhibits bright crimson double flowers.

3. Dianthus 'Valda Kitty' exhibits a compact habit.

4. Dianthus 'Valda Kitty' exhibits dense gray-green foliage.

5. Dianthus 'Valda Kitty' is long flowering, blooming from May to October.

6. Dianthus 'Valda Kitty' is hardy to minus 15° Centigrade.

BRIEF DESCRIPTION OF THE DRAWINGS

The accompanying drawings illustrate the distinguishing traits of the new cultivar.

The drawing on sheet 1 is a color copy of an original photograph showing close-up view of 'Valda Kitty' and illustrating the flower color, foliage color and dense, compact foliage.

The drawing on sheet 2 is a color copy of an original photograph illustrating the flower color of 'Valda Kitty' in comparison to the flower color of the three co-pending varieties. All drawings were made in July of plants grown in 4-inch containers out-of-doors in Encinitas, Calif. All photographs and copies were made using conventional techniques and although colors may appear different from actual colors due to light reflectance they are as accurate as possible by conventional photography and copying.

BOTANICAL DESCRIPTION OF THE PLANT

The following is a detailed description of the new cultivar as grown in a 4-inch container out-of-doors in Arroyo Grande, Calif. The color determinations are in accordance with The Royal Horticultural Society Colour Chart of The Royal Horticultural Society, London, England, except where general color terms of ordinary dictionary significance are used.

Botanical classification: *Dianthus Allwoodii* 'Valda Kitty'.
Commercial classification: Hardy perennial.
Use: Container and landscape plant.
Parentage: 'Valda Kitty' is a sport of Dianthus 'Valda Wyatt' (not patented).
Plant description:
- *Bloom period.*—May to October.
- *Plant habit.*—Dense cushion, compact and clump forming.
- *Height.*—46 cm. in height.
- *Width.*—38 cm. in width.
- *Hardiness.*—Hardy to minus 15° Centigrade.
- *Type.*—Perennial herb.
- *Root system.*—Fibrous.
- *Propagation.*—Propagation is done by cuttings.
- *Cultural requirements.*—Plant in full sun, well-drained and moderately fertile soil.
- *Diseases and pests.*—Susceptible to known Dianthus pests and disease but no other susceptibilities are known to the inventor.
- *Time required to produce roots.*—2 weeks are required to produce roots on initial cutting.
- *Temperature recommended for cuttings to produce roots.*—The air temperature required is 15° Centigrade and the base heat required is 21° Centigrade.
- *Crop time.*—5–7 months are required for a rooted cutting to reach a finished one-gallon container size.

Stem:
- *Shape.*—Cylindrical.
- *Stem dimensions.*—24 cm. in length and 0.25 cm. in diameter.
- *Stem surface.*—Glabrous and glaucous.
- *Stem color.*—189B.
- *Branching.*—Numerous basal breaks.
- *Internode length.*—4–5 cm. between nodes.
- *Node color.*—160D.
- *Node dimensions.*—50 cm. in diameter and 0.50 cm. in height.
- *Lenticels.*—Present.
- *Lenticel dimensions.*—Less than 0.50 mm. in diameter and length.
- *Lenticel color.*—155A.

Foliage:
- *Type.*—Evergreen.
- *Shape.*—Lanceolate.
- *Division.*—Simple.
- *Apex.*—Acute.
- *Base.*—Decurrent.
- *Venation.*—Not Prominent.
- *Margins.*—Entire.
- *Attachment.*—Sheathing.
- *Arrangement.*—Opposite and spiraling up stem.
- *Surface (adaxial and abaxial).*—Glaucous.
- *Leaf dimensions.*—7.5 cm. in length and 0.25 cm. in width.
- *Leaf color (adaxial and abaxial surfaces).*—189A.
- *Fragrance.*—Absent.

Flowers:
- *Type.*—Salviform, double and symmetrical.
- *Flower dimensions.*—4.5 cm. in height and 4.5 cm. in diameter.
- *Throat depth.*—2 cm. in depth.
- *Bud color.*—61A.
- *Bud dimensions.*—4 cm. in length and 1.25 cm. in width.
- *Bud shape.*—Ovate.
- *Petals.*—Persistent, 10–14 double petals, apopetalous, overlapping and synpetalous.
- *Petal margin.*—Crenate.
- *Petal shape.*—Closest to obdeltoid.
- *Petal color (adaxial surface).*—60A.
- *Petal color (abaxial surface).*—61A.
- *Petal surface.*—Glabrous.
- *Calyx dimensions.*—1 cm. in width and 3 cm. in length. Synsepalous, persistent, notched and glabrous.
- *Calyx color.*—138A.
- *Epicalyx color.*—138B.
- *Epicalyx dimensions.*—1 cm. in width and 1 cm. in length.
- *Number of sepals.*—Five.
- *Sepals fused or unfused.*—Fused.
- *Peduncle dimensions.*—9 mm. in length and 3 mm. in diameter.
- *Peduncle color.*—189A.
- *Fragrance.*—Subtle clove scent.
- *Lastingness of flowers.*—5 to 10 days.

Reproductive organs:
- *Stamens.*—Ten, 2 whorls, stamens of outer whorl are shorter, apostemonous, distinct, stamens develop after pistil development, self compatible, exserted 3 mm. above corolla.
- *Stamen dimensions.*—2.5 cm. in length and 1 mm. in diameter.
- *Stamen color.*—155A.
- *Anther attachment.*—Dorsifixed.
- *Anther color.*—57D.
- *Amount of pollen.*—Moderate.
- *Anther dimensions.*—3 mm. in length and 1 mm. in diameter.
- *Pistil.*—One.
- *Pistil color.*—155A.
- *Pistil dimensions.*—2 cm. in length and 1 mm. in diameter.
- *Stigma.*—Two.
- *Stigma color.*—155A.
- *Style color.*—155A.
- *Style dimensions.*—1 cm. in length, 1 mm. in diameter, and exserted 1.0–1.2 cm. above petals.
- *Ovary position.*—Superior.
- *Ovary color.*—155A at base and 139D toward apex.
- *Ovary shape.*—Oval to round.
- *Ovary dimensions.*—7 mm. in height and 6 mm. in diameter.

Seed production: No seed production has been observed.

I claim

1. A new and distinct cultivar of Dianthus plant named 'Valda Kitty', as described and illustrated herein.

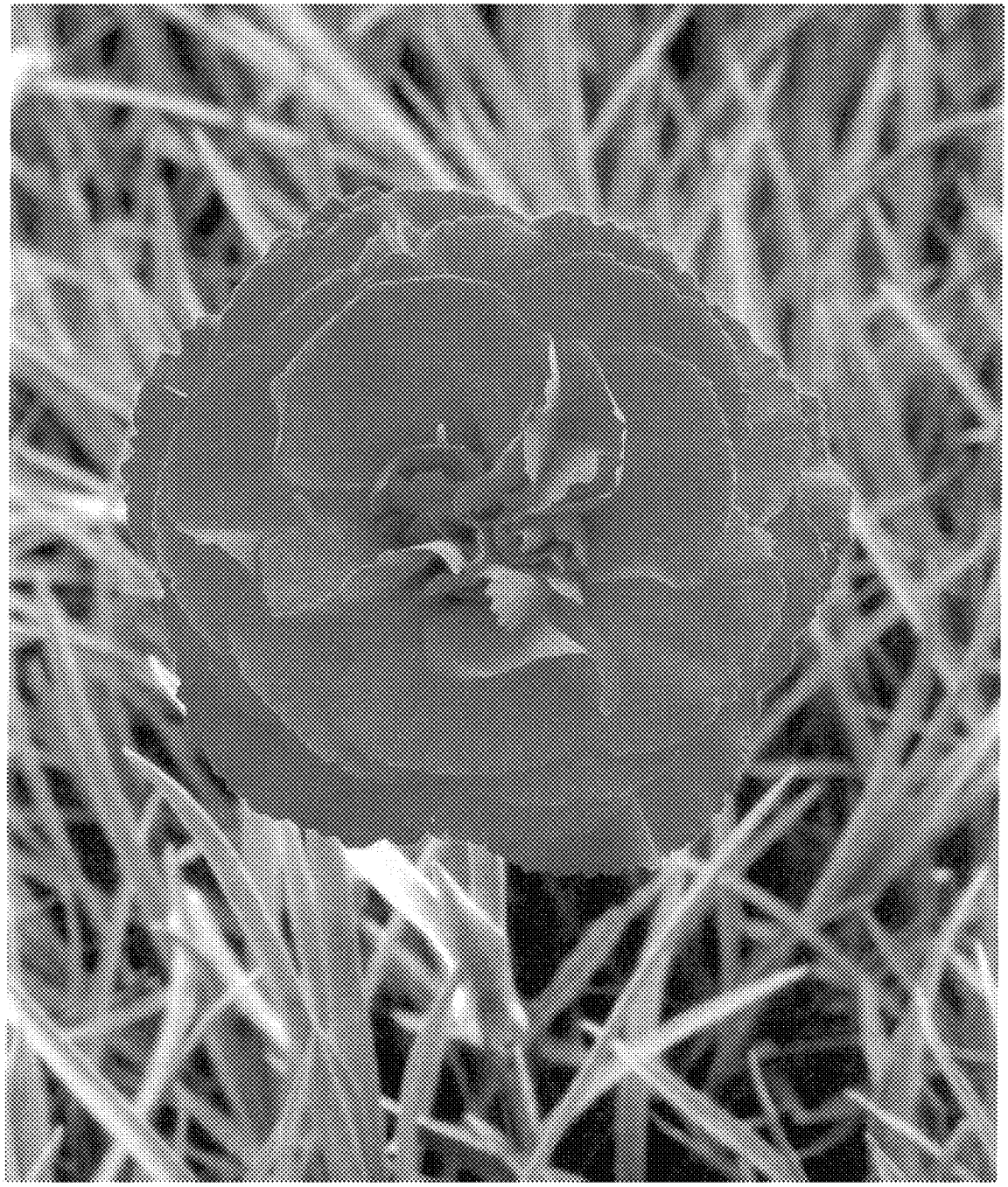

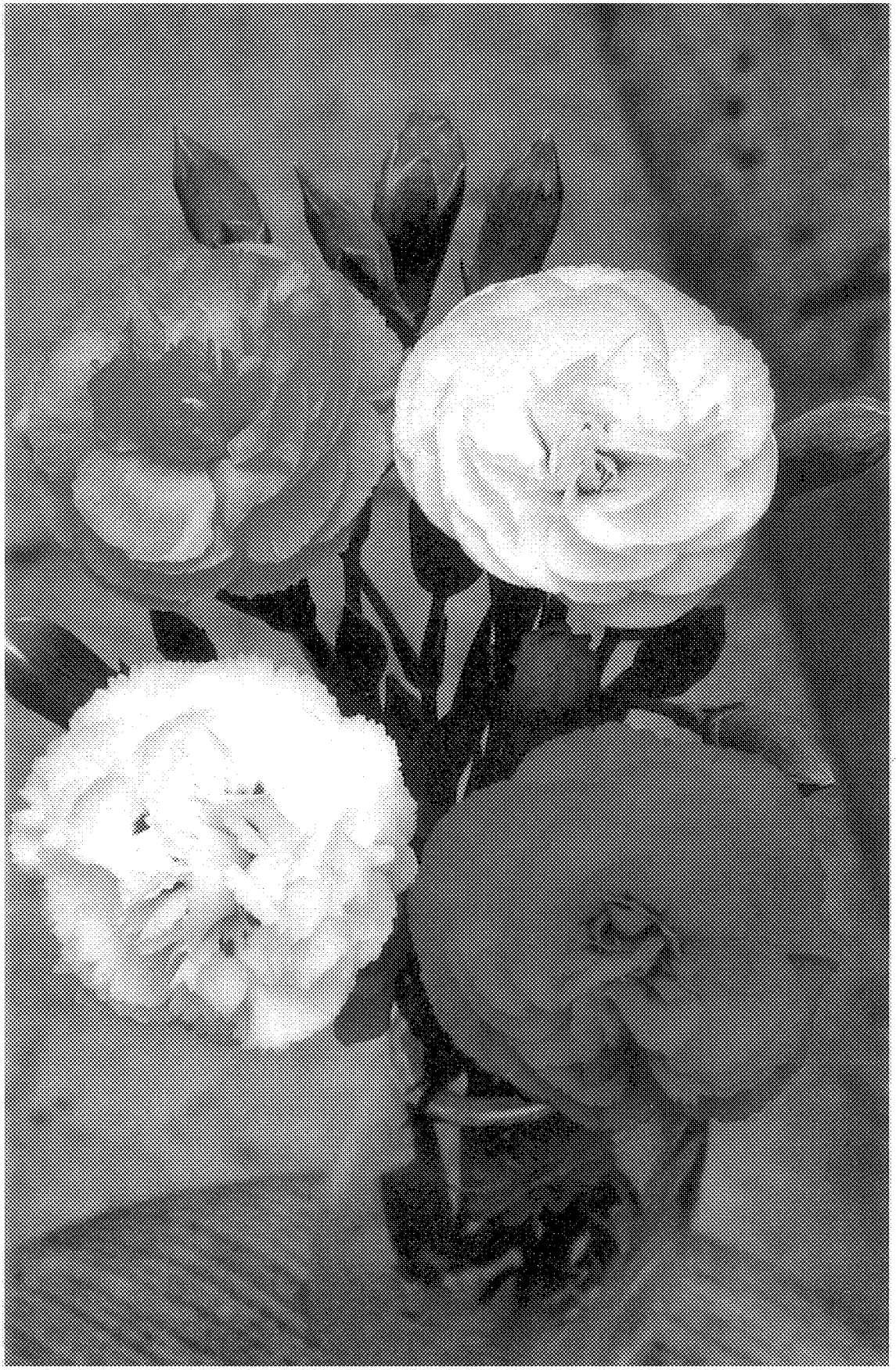

* * * * *